(12) United States Patent
Teng et al.

(10) Patent No.: US 10,646,725 B2
(45) Date of Patent: May 12, 2020

(54) THREE-DIMENSIONAL PRECISE INTRACAVITARY RADIOTHERAPY METHOD AND SYSTEM FOR TREATING TUMOURS

(71) Applicant: NANJING RONGSHENG MEDICAL TECHNOLOGY CO., LTD., Nanjing (CN)

(72) Inventors: Gaojun Teng, Nanjing (CN); Yonghua Dong, Hangzhou (CN); Derong Leng, Nanjing (CN); Jinhe Guo, Nanjing (CN); Chunjun Liu, Nanjing (CN); Haidong Zhu, Nanjing (CN)

(73) Assignee: NANJING RONGSHENG MEDICAL TECHNOLOGY CO., LTD., Nanjing (CN)

( * ) Notice: Subject to any disclaimer, the term of this patent is extended or adjusted under 35 U.S.C. 154(b) by 184 days.

(21) Appl. No.: 15/525,025

(22) PCT Filed: Oct. 23, 2015

(86) PCT No.: PCT/CN2015/092608
§ 371 (c)(1),
(2) Date: May 5, 2017

(87) PCT Pub. No.: WO2016/070721
PCT Pub. Date: May 12, 2016

(65) Prior Publication Data
US 2019/0091486 A1    Mar. 28, 2019

(30) Foreign Application Priority Data
Nov. 7, 2014  (CN) .......................... 2014 1 0626491

(51) Int. Cl.
*A61N 5/10*    (2006.01)
*A61F 2/90*    (2013.01)

(52) U.S. Cl.
CPC .............. *A61N 5/1007* (2013.01); *A61F 2/90* (2013.01); *A61N 2005/1004* (2013.01)

(58) Field of Classification Search
CPC ...... A61F 2250/0067; A61F 2/82; A61F 2/90; A61N 2005/1004; A61N 5/1002;
(Continued)

(56) References Cited

U.S. PATENT DOCUMENTS

2008/0071132 A1* 3/2008 Lamoureux .......... A61N 5/1015
                                                          600/7
2009/0310835 A1* 12/2009 Kaus ..................... G06T 17/20
                                                          382/128
2015/0190654 A1    7/2015 Herskovic

FOREIGN PATENT DOCUMENTS

CN        101161297        4/2008
CN        101455877        6/2009
(Continued)

OTHER PUBLICATIONS https://www.nibib.nih.gov/science-education/science-topics/computed-tomography-ct (accessed Jul. 2013). (Year: 2013).*

*Primary Examiner* — Christine H Matthews
(74) *Attorney, Agent, or Firm* — Kirton McConkie; Evan R. Witt (57) ABSTRACT

Provided in the present invention is a three-dimensional precise intracavitary radiotherapy method and system for treating tumours, comprising the steps of: (1) lesion three-dimensional quantitative measurement and analysis of three-dimensional scanning image of the lesion cavity; (2) comprehensive analysis according to lesion three-dimensional quantitative measurement results and lesion characteristics to calculate the three-dimensional distribution of lesion radiation dose; and (3) according to the three-dimensional distribution diagram of radiation dose, selecting appropriate radiation sources and radiation dose to make a stent, and
(Continued)

performing three-dimensional precise intracavitary radiotherapy. At the same time, also provided by the present invention is a system for achieving the above radiotherapy method. The present invention uses modern medical imaging three-dimensional reconstruction technology for realizing three-dimensional precise internal radiotherapy to treat tumours with an optimized radiation dose and protect normal tissues to an extreme.

9 Claims, 4 Drawing Sheets

(58) Field of Classification Search
CPC ........ A61N 5/1007; G06T 2207/10072; G06T 2207/30096; G06T 7/0012
See application file for complete search history.

(56) References Cited

FOREIGN PATENT DOCUMENTS

| | | |
|---|---|---|
| CN | 101695458 | 4/2010 |
| CN | 104353189 | 2/2015 |
| WO | 2014031950 | 2/2014 |

\* cited by examiner

THREE-DIMENSIONAL PRECISE INTRACAVITARY RADIOTHERAPY METHOD AND SYSTEM FOR TREATING TUMOURS

BACKGROUND

Technical Field

The present invention relates to a three-dimensional precise intracavitary radiotherapy method for treating tumours, and in particular, to a three-dimensional precise intracavitary radiotherapy method for treating tumours, and relates to a three-dimensional precise intracavitary radiotherapy system for treating tumours, and further relates to a fabrication method of an intraluminal radiation stent.

Related Art

With the development of endoscopy and interventional radiology, a minimally invasive ERCP or PTCD method is utilized for cholangiocarcinoma treatment, where external drainage is changed to internal drainage, operations are simple, and survival quality is better than that of a bypass surgery. In 1985, Carrasco fabricated a first extensible metallic bile duct stent, and a better treatment effect is achieved. Similar treatment activities are also gradually carried out since 1990s in China. In a metallic stent bile duct drainage operation, an operation wound is small, a stent with a larger diameter can be implanted by using a thinner catheter, early complications are fewer, and an operative mortality is lower. After a metallic internal stent is implanted into a narrow bile duct, the metallic internal stent can self-expand to an original diameter, and exert a continuous expansion force on a narrow lumen wall, ensuring stability of the stent. There are some limitations to application of a current bile duct stent. For example, the current stent can be used for only palliative treatment, and a long-term curative effect for cholangiocarcinoma has been unoptimistic. Therefore, if a targeted local radiotherapy can be combined with stent expansion, toxic and side effects of total body radiation can be reduced, and better treatment effects can be achieved.

Figures 1, 2, 3:
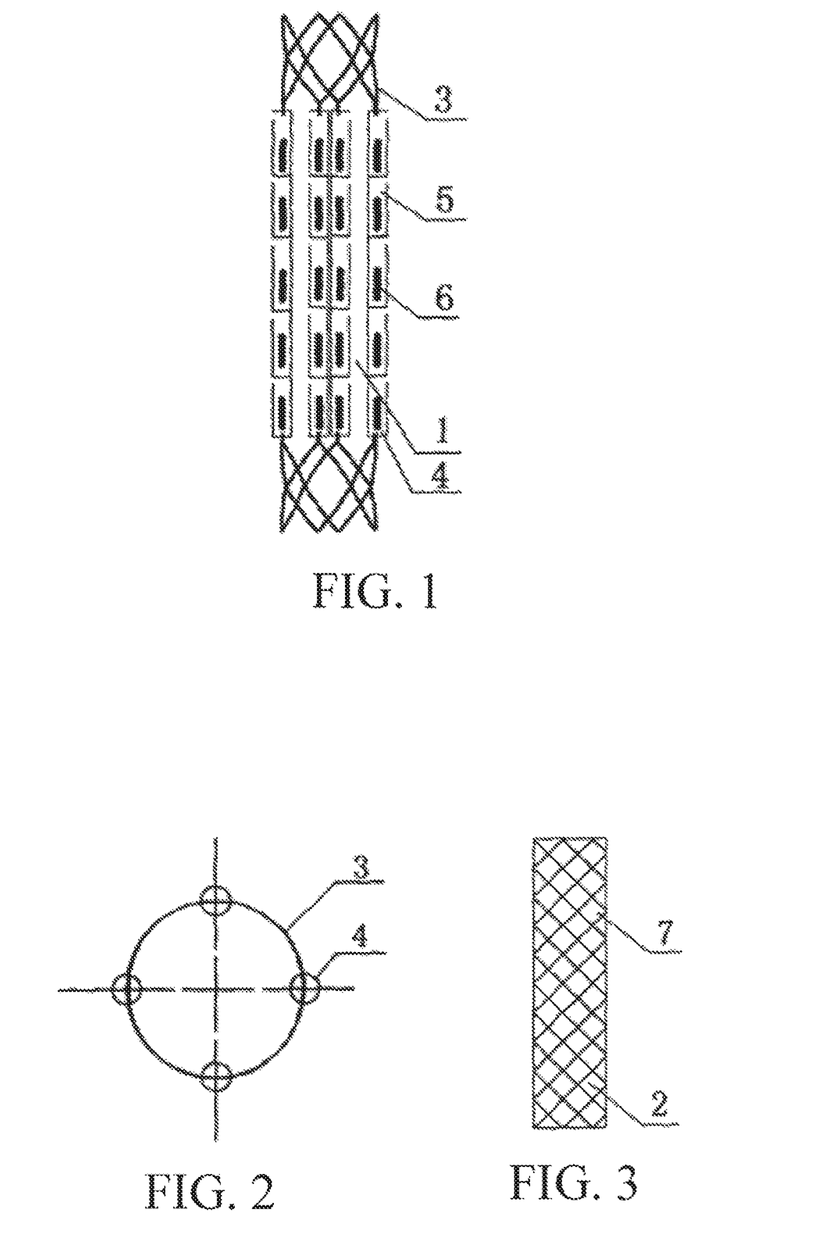
FIG. 1 is a schematic structural diagram of an external stent of an intraluminal radiation stent.
FIG. 2 is a schematic sectional diagram of the external stent of the intraluminal radiation stent.
FIG. 3 is a schematic structural diagram of an internal stent of the intraluminal radiation stent.
Figure 4:
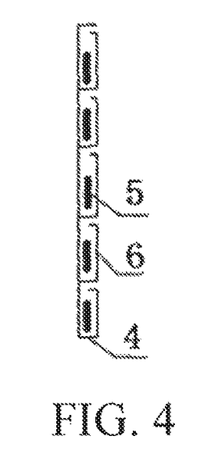
FIG. 4 is a schematic structural diagram of pocket-type radioactive particle filling capsules.
Figure 5:
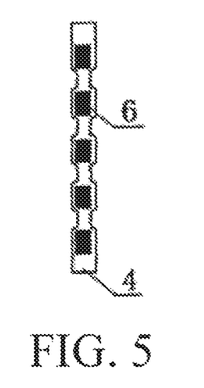
FIG. 5 is a schematic structural diagram of tube-type radioactive particle filling capsules.

To combine expansion of a bile duct and a targeted local radiotherapy, in Chinese Patent Application No. CN101695458A, a bile duct radiation stent is disclosed. A specific structure of the bile duct radiation stent is shown in FIG. 1 to FIG. 5, and includes an external stent 1 and an internal stent 2. The external stent 1 and the internal stent 2 are in a separate state when they are not used, and only when they are used, a main body of the internal stent 2 expends in the external stent 1. As shown in FIG. 3, the main body of the internal stent 2 is a cylindrical skeletal mesh structure 7 woven by nickel-titanium wires. As shown in FIG. 1 and FIG. 2, a main body of the external stent 1 is also a skeletal mesh structure 3 woven by nickel-titanium wires. Radioactive particle filling capsules 4 are mounted on a surface of the skeletal mesh structure 3. The particle filling capsules 4 may be fixed by using barbs (relative to a placing direction) on the surface of the skeletal mesh structure 3, or may be fixed by suturing. Radioactive particle filling capsules 4 may use a small-packet structure 5 with an opening as shown in FIG. 4. The small-packet structure 5 is made of an artificial vascular membrane tube or a polymer tube. An upper portion of the small packet 5 is provided with a small opening to allow a radioactive particle to be placed into and prevent the radioactive particle from exiting. The small pockets 5 are continuously linearly distributed on the surface of the skeletal mesh structure 3, and are axially distributed. Each line of linearly arranged small pockets 5 may be uniformly distributed on the circumferential surface of the skeletal mesh structure 3, or may not be uniformly distributed. The radioactive particle filling capsules 4 may also use a structure shown in FIG. 5. The radioactive particle filling capsules 4 are tubular structures made of plastic heat shrink tubes, and have three-dimensional positioning marks, and a tube diameter at a position at which a radioactive particle is placed is greater than a tube diameter at a position at which a radioactive particle is not placed.

However, the foregoing stenting internal radiotherapy in the prior art is not precise, positions, a dose, and a radioactive source type of radioactive particles are coarsely selected and arbitrarily placed on a stent according to experience of a doctor, rather than determined by a range, a position, and a size of a specific lesion, a viability and a type of tumor cells, and the like. Moreover, for such a placing manner, it is also not considered how to avoid normal tissue in a treated area and protect the normal tissue from radiation of a radiation dose. Consequently, a lesion area is usually not radiated by an appropriate radiation dose, and normal tissue is unnecessarily damaged by radiation. A more precise and efficient stenting intraluminal radiation therapy method and equipment are urgently needed clinically, to overcome the shortcomings in the prior art.

SUMMARY

In view of the disadvantages in the prior art, a first technical problem to be resolved in the present invention is to provide a three-dimensional precise intracavitary radiotherapy method for treating tumours.

Another technical problem to be resolved in the present invention is to provide a three-dimensional precise intracavitary radiotherapy system for treating tumours A further technical problem to be resolved in the present invention is to provide a fabrication method of a three-dimensional precise intraluminal radiation stent for treating tumours.

To achieve the foregoing objectives of the present invention, the following technical solutions are employed in the present invention.

A three-dimensional precise intracavitary radiotherapy method for treating tumours includes the following steps:

step (1): performing three-dimensional quantitative lesion measurement on a three-dimensionally scanned image of a diseased lumen;

step (2): performing comprehensive analysis according to a three-dimensional quantitative lesion measurement result and pathological characteristics, to calculate a three-dimensional radiation dose distribution map of the lesion; and step (3): selecting, according to the three-dimensional radiation dose distribution map of the lesion, appropriate radiation sources and radiation doses to fabricate a stent, and performing three-dimensional precise intraluminal irradiation.

Preferably, in step (1), a process in which three-dimensional reconstruction is performed on the three-dimensionally scanned image of the diseased lumen is included, where tumor tissue and normal tissue are compared, an area of the lesion is drawn at each layer, and finally a three-dimensional structure of locations of the lesion is reconstructed through layer-by-layer superimposition.

Preferably, in step (1), three-dimensional reconstruction is performed on the three-dimensionally scanned image of the diseased lumen in the following manner: first an area of the lesion in each tomographically scanned layer image is drawn according to a density difference in each layer image, and then areas of the lesion in layer images are superimposed in a longitudinal direction, to simulate a three-dimensional structure and a volume of the areas of the lesion.

Preferably, in step (1), three-dimensional reconstruction is performed on the three-dimensionally scanned image of the diseased lumen in the following manner: first an area of the lesion in each tomographically scanned layer image is drawn according to a contrast enhanced tissue difference in each layer image, and then areas of the lesion in layer images are superimposed in a long axis direction, to reconstruct a three-dimensional structure and a volume of the areas of the lesion.

Preferably, in step (1), the three-dimensionally scanned image is one of a type-B ultrasonic image, a CT image, a magnetic resonance imaging scanned image, a PET/CT image, or a PET/MR image.

Preferably, in step (2), the three-dimensional radiation dose distribution map is obtained through comprehensive analysis according to the reconstructed three-dimensional structure in combination with personal information of a patient.

Preferably, in step (3), a method of fabricating the stent includes the following step: placing radioactive particles containing appropriate radiation doses in radioactive particle filling capsules corresponding to locations of the lesion.

Preferably, the stent fabricated in step (3) includes an external stent and an internal stent, the external stent and the internal stent are separate, and a main body of the internal stent expends in the external stent only when the external stent and the internal stent are used; and a main body of the external stent is a skeletal mesh structure, and radioactive particle filling capsules used to place radioactive particles are mounted on a surface of the mesh structure.

A three-dimensional precise intracavitary radiotherapy system for treating tumours, for implementing the foregoing three-dimensional precise intracavitary radiotherapy method, includes:

an image collection module, configured to collect a three-dimensionally scanned image of a diseased lumen;

a three-dimensional quantitative lumen lesion analysis module, configured to determine locations of the lesion;

a radiation dose analysis module, configured to determine radiation sources and radiation doses that are needed for the locations of the lesion; and a stent fabrication module, configured to fabricate a stent that contains radiation sources with corresponding radiation doses at different positions, where the image collection module collects the three-dimensionally scanned image of the lumen lesion, and transmits the three-dimensionally scanned image to the three-dimensional quantitative lumen lesion analysis module for three-dimensional quantitative lesion measurement and analysis; the three-dimensional quantitative lumen lesion analysis module transmits an analysis result to the radiation dose analysis module; the radiation dose analysis module performs comprehensive analysis according to the analysis result and pathological characteristics, to calculate a three-dimensional radiation dose distribution map of the lesion; and the stent fabrication module fabricates the stent according to the three-dimensional radiation dose distribution map, selects radioactive particles with appropriate radiation doses, and places the radioactive particles at corresponding positions on the stent.

Preferably, the three-dimensionally scanned image collected by the image collection module is one of a type-B ultrasonic image, a CT image, a magnetic resonance imaging scanned image, a PET/CT image, or a PET/MR image.

A fabrication method of a three-dimensional precise intraluminal radiation stent for treating tumours includes the following steps:

step (1): performing three-dimensional quantitative lesion measurement on a three-dimensionally scanned image of a diseased lumen;

step (2): performing comprehensive analysis according to a three-dimensional quantitative lesion measurement result and pathological characteristics, to calculate a three-dimensional radiation dose distribution map of the lesion; and step (3): selecting, according to the three-dimensional radiation dose distribution map of the lesion, appropriate radiation sources and radiation doses to fabricate the stent.

Preferably, in step (1), a process in which three-dimensional reconstruction is performed on the three-dimensionally scanned image of the diseased lumen is included, where tumor tissue and normal tissue are compared, an area of the lesion is drawn at each layer, and finally a three-dimensional structure of locations of the lesion is reconstructed through layer-by-layer superimposition.

Preferably, in step (1), three-dimensional reconstruction is performed on the three-dimensionally scanned image of the diseased lumen in the following manner: first an area of the lesion in each tomographically scanned layer image is drawn according to a density difference in each layer image, and then areas of the lesion in layer images are superimposed in a longitudinal direction, to simulate a three-dimensional structure and a volume of the areas of the lesion.

Preferably, in step (1), three-dimensional reconstruction is performed on the three-dimensionally scanned image of the diseased lumen in the following manner: first an area of the lesion in each tomographically scanned layer image is drawn according to a contrast enhanced tissue difference in each layer image, and then areas of the lesion in layer images are superimposed in a long axis direction, to reconstruct a three-dimensional structure and a volume of the areas of the lesion.

Preferably, in step (1), the three-dimensionally scanned image is one of a type-B ultrasonic image, a CT image, a magnetic resonance imaging scanned image, a PET/CT image, or a PET/MR image.

Preferably, in step (2), the three-dimensional radiation dose distribution map is obtained through comprehensive analysis according to the reconstructed three-dimensional structure in combination with personal information of a patient.

Preferably, in step (3), a method of fabricating the stent includes the following step: placing radioactive particles containing appropriate radiation doses in radioactive particle filling capsules corresponding to locations of the lesion.

Preferably, the stent fabricated in step (3) includes an external stent and an internal stent, the external stent and the internal stent are separate, and a main body of the internal stent expends in the external stent only when the external stent and the internal stent are used; and a main body of the external stent is a skeletal mesh structure, and radioactive particle filling capsules used to place radioactive particles are mounted on a surface of the mesh structure.

A three-dimensional precise intraluminal radiation stent is fabricated according to the foregoing fabrication method.

Compared with the prior art, the present invention has the following beneficial effects:

In the present invention, three-dimensional reconstruction is performed on diseased tissue of a diseased lumen by utilizing a modern three-dimensional medical image reconstruction technology, and a pathological type, a metabolic activity, and a sensitivity to a radioactive ray of the diseased tissue are comprehensively evaluated by applying a contrast imaging enhancement technology and a pathological tissue examination technology, to provide an optimal three-dimensional radiation treatment dose distribution map for each diseased lumen of a patient. In this way, in a process of fabricating a stent, most appropriately optimized radioactive treatment particles are placed at suitable positions on the stent, to treat a tumor with an optimal radiation dose and achieve three-dimensional precise intraluminal irradiation, and to protect normal tissue to the greatest extent.

DETAILED DESCRIPTION

Technical content of the present invention is further described in detail below with reference to the accompanying drawings and specific embodiments.

Figure 6:
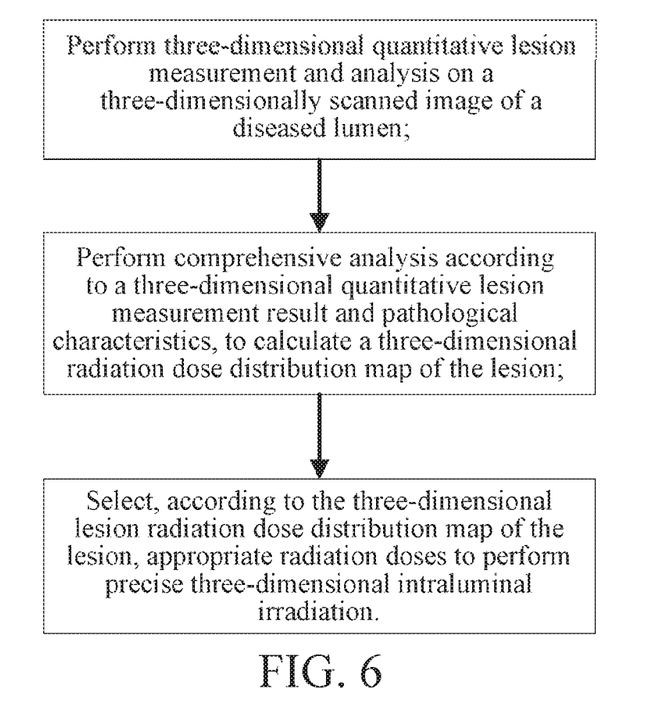
FIG. 6 is a flowchart of a three-dimensional precise intracavitary radiotherapy method for treating tumours according to the present invention.

The present invention first provides a three-dimensional precise intracavitary radiotherapy method for treating tumours, as shown in FIG. 6, including the following steps:

step (1): performing three-dimensional quantitative lesion measurement and analysis on a three-dimensionally scanned image of a diseased lumen;

step (2): performing comprehensive analysis according to a three-dimensional quantitative lesion measurement result and pathological characteristics, to calculate a three-dimensional radiation dose distribution map of the lesion; and step (3): selecting, according to the three-dimensional lesion radiation dose distribution map of the lesion, appropriate radiation sources and radiation doses to fabricate a stent, and performing three-dimensional precise intraluminal irradiation.

Figure 7:
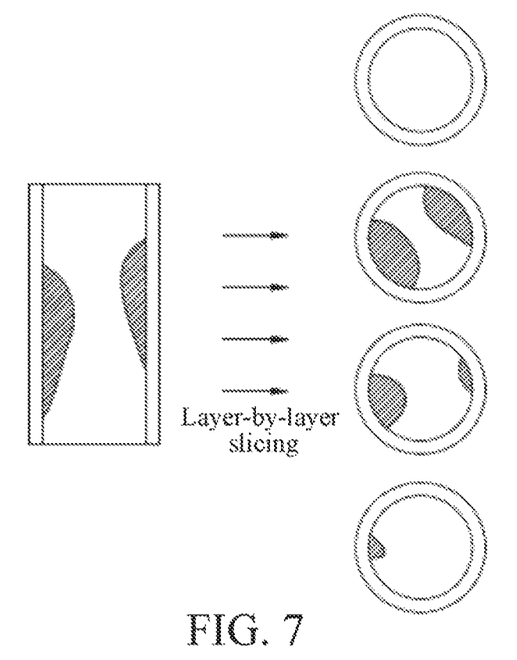
FIG. 7 is a schematic diagram of multiple-layer lesion slicing according to an embodiment of the present invention.

First, in step (1), as shown in FIG. 7, a three-dimensional quantitative lumen lesion analysis module performs three-dimensional quantitative lesion measurement and analysis on the diseased lumen according to the three-dimensionally scanned image (including but not limited to a type-B ultrasonic image, a CT image, a magnetic resonance imaging scanned image, a PET/CT image, or a PET/MR image). It is intended to perform three-dimensional reconstruction on diseased tissue of the diseased lumen by using a modem three-dimensional medical image reconstruction technology. Specifically, the following two implementation manners are included.

A first manner: First an area of the lesion in each tomographically scanned layer image such as a CT image or an MR image is drawn by using a three-dimensional quantitative lumen lesion analysis system according to a density difference in each layer image, referring to FIG. 7; and then areas of the lesion in layer images are superimposed in a longitudinal direction, to simulate a three-dimensional structure and a volume of the areas of the lesion.

A second manner: First an area of the lesion in each tomographically scanned layer image such as a CT image or an MR image is drawn by using a three-dimensional quantitative lumen lesion analysis system according to a contrast enhanced tissue difference in each layer image, referring to FIG. 7; and then areas of the lesion in layer images are superimposed in a long axis direction, to reconstruct a three-dimensional structure and a volume of the areas of the lesion.

Figure 8:
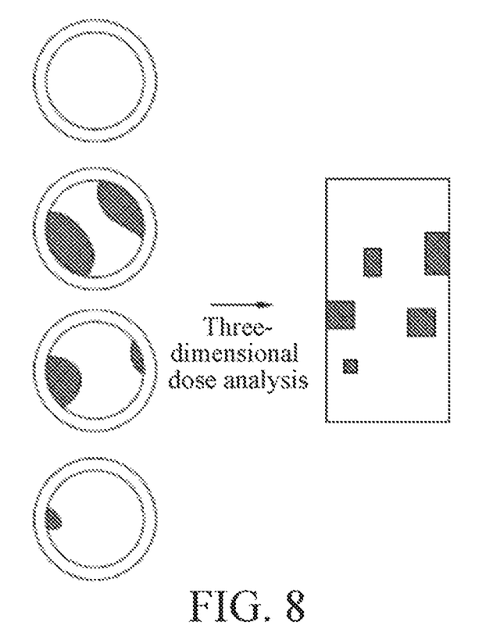
FIG. 8 is a schematic diagram of a three-dimensional radiation dose distribution obtained according to lesion slicing shown in FIG. 7.

Then, in step (2), as shown in FIG. 8, a radiation dose analysis module performs comprehensive analysis according to a three-dimensional quantitative lesion measurement result and pathological characteristics, to calculate a three-dimensional radiation dose distribution map of the lesion, and a pathological type, a metabolic activity, and a sensitivity to a radioactive ray of the diseased tissue are comprehensively evaluated by mainly applying a contrast imaging enhancement technology and a pathological tissue examination technology, to provide an optimal three-dimensional radiation treatment dose distribution map for each diseased lumen of a patient.

Figure 9:
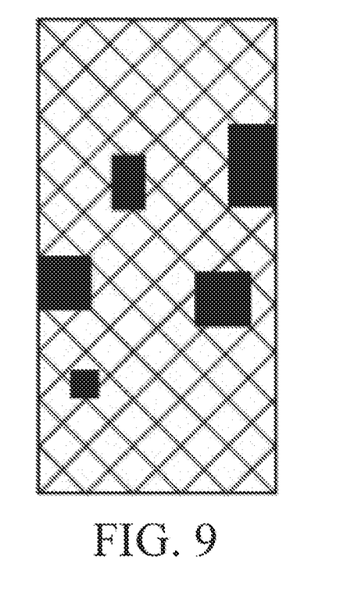
FIG. 9 is a schematic diagram of placing different doses of radioactive particles at different positions on a stent according to the schematic diagram of the three-dimensional radiation dose distribution shown in FIG. 8.

Finally, in step (3), a stent that contains radiation sources with corresponding radiation doses at different positions is fabricated according to the three-dimensional radiation dose distribution map of the lesion. That is, as shown in FIG. 9, radioactive particles containing appropriate radiation doses are placed in radioactive particle filling capsules corresponding to locations of the lesion.

In the present invention, by means of reconstruction and radiation dose calculation, a tumor is treated with optimal radiation sources and radiation doses, normal tissue can be protected to the greatest extent, and three-dimensional precise intraluminal radiation can be achieved.

Figure 10:
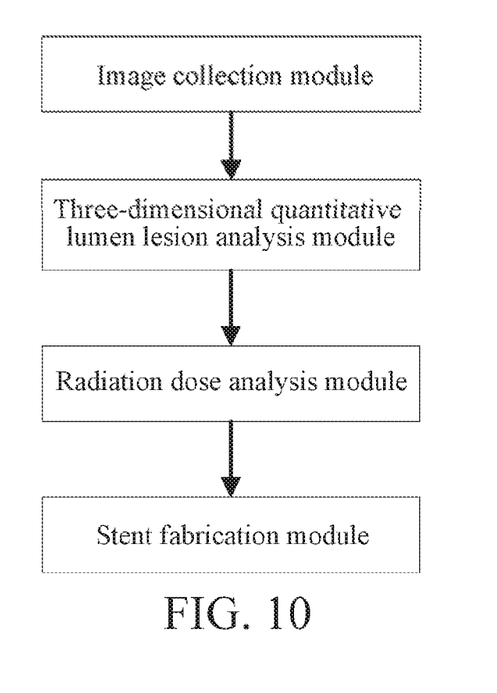
FIG. 10 is a schematic structural diagram of a three-dimensional precise intracavitary radiotherapy system for treating tumours according to the present invention.

The present invention further provides a three-dimensional precise intracavitary radiotherapy system for treating tumours, referring to FIG. 10, including an image collection module, a three-dimensional quantitative lumen lesion analysis module, a radiation dose analysis module, and a stent fabrication module.

The image collection module collects a three-dimensionally scanned image of a lumen lesion, where the collected three-dimensionally scanned image includes but is not limited to one of a type-B ultrasonic image, a CT image, a magnetic resonance imaging scanned image, a PET/CT image, or a PET/MR image, and transmits the three-dimensionally scanned image to the three-dimensional quantitative lumen lesion analysis module for three-dimensional quantitative lesion measurement; the three-dimensional quantitative lumen lesion analysis module then transmits a measurement result to the radiation dose analysis module; the radiation dose analysis module performs comprehensive analysis according to the analysis result and pathological characteristics, to calculate a three-dimensional radiation dose distribution map of the lesion; and the stent fabrication module fabricates a stent according to the three-dimensional radiation dose distribution map, selects radioactive particles with appropriate radiation doses, and places the radioactive particles at corresponding positions on the stent.

Specifically, the three-dimensional quantitative lumen lesion analysis module first draws an area of the lesion in each tomographically scanned layer image such as a CT image or an MR image according to a density difference in each layer image, and then superimposes areas of the lesion in layer images in a longitudinal direction, to simulate a three-dimensional structure and a volume of the areas of the lesion. Alternatively, the three-dimensional quantitative lumen lesion analysis system first draws an area of the lesion in each tomographically scanned layer image such as a CT image or an MR image according to a contrast enhanced tissue difference in each layer image, and then superimposes areas of the lesion in layer images in a long axis direction, to reconstruct a three-dimensional structure and a volume of the areas of the lesion.

The radiation dose analysis module performs systematic and comprehensive analysis and optimization according to a lesion size, a cell activity degree, a cell metabolic level, a cell malignant transformation degree, a sensitive degree to a radioactive ray, and the like of parts and directions of the lesion, and provides an optimal three-dimensional radiation dose distribution map. A radioactive particle tilling module places radioactive particles on an external surface of an external stent according to the optimal three-dimensional radiation dose distribution map. Finally, the foregoing stent on which the radioactive particles are placed is mounted into a releaser to implant the stent by using the releaser. By using a conventional interventional operation method of releasing the mounted stent, the stent is released into the diseased lumen. In a release process, an orientation of the stent may be adjusted according to three-dimensional space markers opaque to an X ray that are placed on the stent, so that a three-dimensional orientation of the radiation stent is consistent with a three-dimensional orientation of the lesion.

In the present invention, a stent structure formed by two separate stent bodies (an internal stent and an external stent) is used, and the internal stent and the external stent are implanted in different steps, so that the stent bodies can be loaded into a smaller implanter, making it possible to implant a bile duct stent carrying radioactive particles, and bringing a lower risk and less suffering of a patient. Moreover, such a stent has a simple structure, is easy to manufacture, and can be reliably fixed in a lumen. By means of expansion of the internal stent, the external stent carrying radioactive particles can be fixed on a surface of the internal stent and does not slide. For a specific structure of the stent, refer to the description in the background section.

A method of implanting the stent is as follows: The external stent with filled radioactive particles is conducted into a body, and the external stent is released with guidance of a guide wire or with assistance of an endoscope, and then the internal stent is conducted and released with guidance of a guide wire or with assistance of an endoscope; after the stents are implanted, the internal stent expands to expand the external stent and expand narrow parts of the lumen, fixing the external stent to prevent movement.

The three-dimensional precise intracavitary radiotherapy system and method for treating tumours are described in detail below by using different embodiments.

In Embodiment 1, after a patient is diagnosed with esophageal carcinoma and needs three-dimensional precise intraluminal irradiation, a first step is to perform three-dimensional reconstruction on a CT/MR image of the patient by using the three-dimensional quantitative lumen lesion analysis module provided in the present invention. The analysis module may draw an area of a lesion at each layer by using differences of tumor tissue and normal surrounding tissue in density, form, contrast agent enhancement, and other aspects, and reconstruct a three-dimensional structure of the tumor through layer-by-layer superimposition.

Then, the reconstructed three-dimensional structure of the tumor lesion and related information such as a pathological type of the tumor, whether blood vessels are rich, and an age and body conditions of the patient are input to the radiation dose analysis module provided in the present invention. The system comprehensively analyzes the various information, to design a three-dimensional radiation dose distribution map and appropriate radiation source types.

Radioactive particles are placed on the surface of the external stent 1 according to the three-dimensional radiation dose distribution map designed by the radiation dose analysis module and matched three-dimensional positions.

During use, first, radioactive particles 6 are placed into the radioactive particle filling capsules 4. The radioactive particles 6 may use a common medical radioactive material such as $^{103}$Pd, $^{60}$Co, $^{199}$Au, $^{192}$Ir, or $^{125}$I. Then the external stent 1 with the filled radioactive particles 6 is again loaded into an implanter, and the external stent 1 is released with guidance of a guide wire or with assistance of an endoscope. Then the internal stent 2 is released with guidance of a guide wire or with assistance of an endoscope. The internal stent 2 is outside the external stent 1, and expands the external stent 1 and at the same time expands narrow parts of an esophageal, fixing the external stent 1 to prevent it from moving. In an actual fabrication process, the radioactive particle filling capsules 4 may be filled with a stripe-like, a column-like, or a hall-like radioactive nuclide according to requirements. The internal stent 2 is a mesh cylinder woven by nickel-titanium wires. The stent in the present invention can generate radioactive rays by carrying radio sources, and not only can kill tumor cells and inhibit proliferation of the tumor cells through local irradiation, but also can maintain smoothness of the esophageal through radial support of the stent, so that intraluminal radiation and narrowness expansion treatment are combined, and a tumor is inhibited or inactivated and an occurrence rate that the esophageal is narrow again after the stent is implanted. A separate structure design is used. A diameter of a conductor matching such type of stent is efficiently reduced through double implantation, thereby resolving a problem that a diameter of a conductor is excessively large when radiation particles and a stent are implanted together, and making it possible to implant an esophageal stent carrying radiation particles.

In Embodiment 2, after a patient is diagnosed with cholangiocarcinoma and needs three-dimensional precise intraluminal irradiation, a first step is to perform three-dimensional reconstruction on a CT/MR image of the patient by using the three-dimensional quantitative lumen lesion analysis module provided in the present invention. The analysis module may draw an area of a lesion at each layer by using differences of tumor tissue and normal surrounding tissue in density, form, contrast agent enhancement, and other aspects, and reconstruct a three-dimensional structure of the tumor through layer-by-layer superimposition.

Then, the reconstructed three-dimensional structure of the tumor lesion and related information such as a pathological type of the tumor, whether blood vessels are rich, and an age and body conditions of the patient are input to the radiation dose analysis module provided in the present invention. The radiation dose analysis module comprehensively analyzes the various information, to design a three-dimensional radiation dose distribution map and appropriate radiation source types. Radioactive particles are placed on the surface of the external stent 1 according to matched three-dimensional positions.

During use, first, radioactive particles 6 are placed into the radioactive particle filling capsules 4. The radioactive particles 6 may use a common medical radioactive material such as $^{103}$Pd $^{60}$Co, $^{199}$Au, $^{192}$Ir, or $^{125}$I. Then the external stent 1 with the filled radioactive particles 6 is again loaded into an implanter, and the external stent 1 is released with guidance of a guide wire or with assistance of an endoscope. Then the internal stent 2 is released with guidance of a guide wire or with assistance of an endoscope. The internal stent 2 is outside the external stent 1, and expands the external stent 1 and at the same time expands narrow parts of a bile duct, fixing the external stent 1 to prevent it from moving. The radioactive particle filling capsules 4 may be filled with a stripe-like, a column-like, or a ball-like radioactive nuclide according to requirements. The internal stent 2 is a mesh cylinder woven by nickel-titanium wires.

In addition, it should be noted that, in the three-dimensional precise intracavitary radiotherapy method for treating tumours provided above, a process is essentially how to fabricate a precise intraluminal stent, and perform intraluminal radiation by using the stent for which corresponding radioactive particles are placed at positions of a lesion. Therefore, the present invention also provides a fabrication method of a three-dimensional precise intraluminal radiation stent for treating tumours, specifically referring to FIG. 6, including the following steps:

step (1): performing three-dimensional quantitative lesion measurement and analysis on a three-dimensionally scanned image of a diseased lumen;

step (2): performing comprehensive analysis according to a three-dimensional quantitative lesion measurement result and pathological characteristics, to calculate a three-dimensional radiation dose distribution map of the lesion; and step (3): selecting, according to the three-dimensional radiation dose distribution map of the lesion, appropriate radiation sources and radiation doses to fabricate the stent.

First, in step (1), as shown in FIG. 7, a three-dimensional quantitative lumen lesion analysis module performs three-dimensional quantitative lesion measurement and analysis on the diseased lumen according to the three-dimensionally scanned image (including but not limited to a type-B ultrasonic image, a CT image, a magnetic resonance imaging scanned image, a PET/CT image, or a PET/MR image). Three-dimensional reconstruction is performed on diseased tissue of the diseased lumen by using a modem three-dimensional medical image reconstruction technology. Specifically, the following two implementation manners are included.

A first manner: First an area of the lesion in each tomographically scanned layer image such as a CT image or an MR image is drawn by using a three-dimensional quantitative lumen lesion analysis system according to a density difference in each layer image, referring to FIG. 7; and then areas of the lesion in layer images are superimposed in a longitudinal direction, to simulate a three-dimensional structure and a volume of the areas of the lesion.

A second manner: First an area of the lesion in each tomographically scanned layer image such as a CT image or an MR image is drawn by using a three-dimensional quantitative lumen lesion analysis system according to a contrast enhanced tissue difference in each layer image, referring to FIG. 7; and then areas of the lesion in layer images are superimposed in a long axis direction, to reconstruct a three-dimensional structure and a volume of the areas of the lesion.

Then, in step (2), as shown in FIG. 8, a radiation dose analysis module performs comprehensive analysis according to a three-dimensional quantitative lesion measurement result and pathological characteristics, to calculate a three-dimensional radiation dose distribution map of the lesion, and a pathological type, a metabolic activity, and a sensitivity to a radioactive ray of the diseased tissue are comprehensively evaluated by mainly applying a contrast imaging enhancement technology and a pathological tissue examination technology, to provide an optimal three-dimensional radiation treatment dose distribution map for each diseased lumen of a patient.

Finally, in step (3), as shown in FIG. 9, a stent that contains radiation sources with corresponding radiation doses at different positions is fabricated according to the three-dimensional radiation dose distribution map of the lesion. In short, radiation sources may be distributed on a fabricated internal stent by placing radioactive particles containing appropriate radiation doses in radioactive particle filling capsules corresponding to locations of the lesion. In other fabrication methods not mentioned in detail in this specification, an external stent containing radioactive particles may also be fabricated by using other technological means such as 3D printing.

The stent provided in the present invention can generate radioactive rays by carrying radio sources, and not only can kill tumor cells and inhibit proliferation of the tumor cells through local irradiation, but also can maintain smoothness of the bile duct through radial support of the stent, so that intraluminal radiation and narrowness expansion treatment are combined, and a tumor is inhibited or inactivated and an occurrence rate that the bile duct is narrow again after the stent is implanted. In addition, a separate structure design including an internal stent and an external stent is used. A diameter of a conductor matching such type of stent is efficiently reduced through double implantation, thereby resolving a problem that a diameter of a conductor is excessively large when radiation particles and a stent are implanted together and the radiation particles and the stent cannot pass through a biopsy channel of a duodenoscope, and making it possible to implant an intraluminal radiation stent carrying radiation particles.

To sum up, in the present invention, three-dimensional reconstruction is performed on diseased tissue of a diseased lumen by utilizing a modern three-dimensional medical image reconstruction technology, and a pathological type, a metabolic activity, and a sensitivity to a radioactive ray of the diseased tissue are comprehensively evaluated by applying a contrast imaging enhancement technology and a pathological tissue examination technology, to provide an optimal three-dimensional radiation treatment dose distribution map for each diseased lumen of a patient. In this way, in a process of fabricating a stent, most appropriately optimized radioactive treatment particles are placed at suitable positions on the stent, achieving three-dimensional precise intraluminal irradiation. In addition, by filling radioactive particles during operation, a speed is fast, and radiation received by a doctor in an operation process can be reduced. By means of the three-dimensional precise intracavitary radiotherapy method for treating tumours, a tumor can be treated with an optimal radiation dose, and normal tissue can be protected to the greatest extent.

The three-dimensional precise intracavitary radiotherapy system for treating tumours and method thereof provided in the present invention are described in detail above. Any obvious modifications to the present invention by a person of skilled in the art without departing from the essential spirit of the present invention shall constitute an infringement of patent right of the present invention, and the person shall bear corresponding legal liability.

What is claimed is:

1. A three-dimensional precise intracavitary radiotherapy method for treating tumours, comprising the following steps:
    step (1): performing three-dimensional quantitative lesion measurement on multiple three-dimensionally scanned images of a diseased lumen;
    step (2): performing comprehensive analysis according to a three-dimensional quantitative lesion measurement result and pathological characteristics, to calculate a three-dimensional radiation dose distribution map of the diseased lumen; and
    step (3): according to the three-dimensional radiation dose distribution map of the diseased lumen, selecting appropriate radiation sources and radiation doses to fabricate a stent, fabricating the stent and performing three-dimensional precise intraluminal irradiation by using the stent;
    the stent fabricated in step (3) comprising an external stent and an internal stent, the external stent and the internal stent being separate, and a main body of the internal stent expanding in the external stent only when the external stent and the internal stent are used; and a main body of the external stent being skeletal a mesh structure, and multiple radioactive particle filling capsules used to place radioactive particles being mounted on a surface of the mesh structure.

2. The three-dimensional precise intracavitary radiotherapy method for treating tumours according to claim 1, wherein
    in step (1), three-dimensional reconstruction is performed on the three-dimensionally scanned images of the diseased lumen; wherein, each three-dimensionally scanned image is a tomographically scanned image, an area of a lesion is drawn at each three-dimensionally scanned image by comparing tumor tissue and normal tissue, and finally a three-dimensional structure of locations of the lesion is reconstructed through layer-by-layer superimposition of all three-dimensionally scanned images.

3. The three-dimensional precise intracavitary radiotherapy method for treating tumours according to claim 2, wherein
    in step (1), the three-dimensional reconstruction is performed on the three-dimensionally scanned images of the diseased lumen in the following manner: first the area of the lesion in each tomographically scanned image is drawn according to a density difference in each tomographically scanned image, and then areas of the lesion in all tomographically scanned images are superimposed in a longitudinal direction, to simulate a three-dimensional structure and a volume of the areas of the lesion.

4. The three-dimensional precise intracavitary radiotherapy method for treating tumours according to claim 2, wherein
    in step (1), the three-dimensional reconstruction is performed on the three-dimensionally scanned images of the diseased lumen in the following manner: first the area of the lesion in each tomographically scanned image is drawn according to a contrast enhanced tissue difference in each tomographically scanned image, and then areas of the lesion in all tomographically scanned images are superimposed in a long axis direction, to reconstruct a three-dimensional structure and a volume of the areas of the lesion.

5. The three-dimensional precise intracavitary radiotherapy method for treating tumours according to claim 1, wherein
    in step (1), the three-dimensionally scanned images are one of a type-B ultrasonic image, a CT image, a magnetic resonance imaging scanned image, a PET/CT image, or a PET/MR image.

6. The three-dimensional precise intracavitary radiotherapy method for treating tumours according to claim 2, wherein
    in step (2), the three-dimensional radiation dose distribution map is obtained through comprehensive analysis according to the reconstructed three-dimensional structure in combination with personal information of a patient.

7. The three-dimensional precise intracavitary radiotherapy method for treating tumours according to claim 1, wherein
    in step (3), fabricating the stent comprises the following step: placing the radioactive particles, containing the appropriate radiation doses, in the radioactive particle filling capsules corresponding to locations of the lesion.

8. A three-dimensional precise intracavitary radiotherapy system for treating tumours, for implementing the three-dimensional precise intracavitary radiotherapy method according to claim 1, comprising:
    an image collection module, configured to collect the three-dimensionally scanned images of the diseased lumen;
    a three-dimensional quantitative lumen lesion analysis module, configured to determine locations of the lesion;
    a radiation dose analysis module, configured to determine the radiation sources and the radiation doses that are needed for the locations of the lesion; and
    a stent fabrication module, configured to fabricate a stent that contains the radiation sources with corresponding radiation doses at different positions, wherein
    the image collection module collects the three-dimensionally scanned images of the diseased lumen, and transmits the three-dimensionally scanned images to the three-dimensional quantitative lumen lesion analysis module for three-dimensional quantitative lesion measurement and analysis; the three-dimensional quantitative lumen lesion analysis module transmits an analysis result to the radiation dose analysis module; the radiation dose analysis module performs comprehensive analysis according to the analysis result and pathological characteristics, to calculate the three-dimensional radiation dose distribution map of the diseased lumen; and the stent fabrication module fabricates the stent according to the three-dimensional radiation dose distribution map, selects the radioactive particles with the appropriate radiation doses, and places the radioactive particles at corresponding positions on the stent.

9. The three-dimensional precise intracavitary radiotherapy system for treating tumours according to claim 8, wherein
    the three-dimensionally scanned images collected by the image collection module are one of a type-B ultrasonic image, a CT image, a magnetic resonance imaging scanned image, a PET/CT image, or a PET/MR image.

* * * * *